United States Patent [19]

O'Sullivan et al.

[11] Patent Number: 4,904,764
[45] Date of Patent: Feb. 27, 1990

[54] 4-DIAZO-3-METHYL-2,5-CYCLOHEXADINE-1-ONE AND PHARMACETICALLY ACCEPTABLE SALTS THEREOF

[75] Inventors: Joseph O'Sullivan, Belle Mead; Pushpa Singh, Piscataway, both of N.J.

[73] Assignee: E. R. Squibb & Sons, Inc., Princeton, N.J.

[21] Appl. No.: 808,146

[22] Filed: Dec. 12, 1985

[51] Int. Cl.$^4$ .................. C07C 113/04; A61K 31/665
[52] U.S. Cl. ..................................... 534/564; 514/150; 534/558; 534/565; 435/41; 435/128; 435/933
[58] Field of Search ............................... 534/556, 564

[56] References Cited

PUBLICATIONS

Chem. Ber., vol. 95, pp. 1206–1218, (1962).

Houben–Weyl, Methoden Der Organischen Chemie, *Chinondiazide*, pp. 353–394, (1979).
Horner et al., Ber. Deut, Chem. Gesell., vol. 95, pp. 1206 to 1218, (1962).
Poskocil et al., Chemical Abstracts, vol. 48, #4221a–t, (1954).

*Primary Examiner*—Floyd D. Higel
*Attorney, Agent, or Firm*—Donald J. Barrack; Timothy J. Gaul

[57] ABSTRACT

4-Diazo-3-methoxy-2,5-cyclohexandien-1-one, and pharmaceutically acceptable salts thereof, are antibiotics having antibacterial activity against a variety of gram positive and gram negative bacteria, particularly against anaerobic bacteria. The compound can be prepared by culturing aerobically *Penicillium funiculosum* A.T.C.C. No. 20783 in a culture medium containing assimilable sources of carbohydrates and nitrogen.

2 Claims, No Drawings

4-DIAZO-3-METHYL-2,5-CYCLOHEXADINE-1-ONE AND PHARMACETICALLY ACCEPTABLE SALTS THEREOF

SUMMARY OF THE INVENTION

Cultivation of a strain of the microorganism, *Penicillium funiculosum*, that has been deposited in the American Type Culture Collection as A.T.C.C. No. 20783, yields a novel antibiotic substance, 4-diazo-3-methoxy-2,5-cyclohexadien-1-one. The antibiotic has also been synthesized chemically. 4-Diazo-3-methoxy-2,5-cyclohexadien-1-one has the following structure:

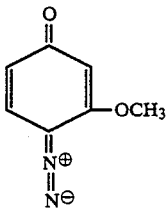

The antibiotic has activity against a variety of gram positive and gram negative bacteria, particularly against anaerobic bacteria, and can be used to combat bacterial infections in mammalian species such as humans and domesticated animals.

DETAILED DESCRIPTION OF THE INVENTION

The Microorganism

The microorganism used for the production of 4-diazo-3-methoxy-2,5-cyclohexadien-1-one is a strain of *Penicillium funiculosum*, isolated from a sample obtained in Princeton, N.J. A subculture of the organism can be obtained from the American Type Culture Collection, Rockville, Md. Its accession number in this repository is A.T.C.C. No. 20783. In addition to the specific microorganism described and characterized herein, it should be understood that mutants of the microorganism produced through the use of chemical or physical mutagens can also be cultivated to produce the product.

The culture of *Penicillium funiculosum* was isolated from a mushroom (Marasmius, member of the Agaricaceae) on which it was present. The air-dried mushroom was cut into pieces with a sterile scalpel and ground to a powder with a sterile mortar and pestle. A sterile Dispo Plug (American Scientific Products, McGaw Park, Ill.) was dipped into the powder and then pressed onto the surface of an agar medium in a petri dish at 10 to 12 different sites. This was repeated on several agar containing petri dishes without reloading the plug with powder, thus effecting a dilution of the microflora in the powder and enabling the isolation of isolated colonies. This same technique can be used to isolate the microorganism from soil samples in which it is present.

The nutrient agar used in this process has the following composition:

| | |
|---|---|
| $KH_2PO_4$ | 1.0 grams |
| $MgSO_4.7H_2O$ | 0.5 grams |
| Peptone | 5.0 grams |
| Dextrose | 10.0 grams |

-continued

| | |
|---|---|
| Agar | 20.0 grams |

The medium, after sterilization in an autoclave at 121° C. for 30 minutes, is supplemented with filter-sterilized solutions of rose bengal and streptomycin to yield final concentrations of 34 to 30 µg/ml, respectively.

After 4 days incubation at 25° C., colonies of *Penicillium funiculosum* A.T.C.C. No. 20783 are isolated from the plated sample. The isolated colonies are picked off and maintained on Potato-Dextrose agar (Difco).

Colonies of *Penicillium funiculosum* A.T.C.C. No. 20783 on Czapek's agar grow to 5–6 cm in 14 days. Growth is azonate with a marked tendency to form aerial ropes of hyphae (funiculose) interspersed with wooly (floccose) areas. The reverse color ranges from yellow to orange or red. Sporulation on this medium is scant; sporulation is good on malt agar.

Conidiophores arise perpendicularly to the funiculose hyphae. In the marginal areas, they arise directly from the substrate hyphae. They terminate in biverticillate, symmetric penicilli bearing dark green to bluish conidial heads. The conidia are produced in chains from clusters of lanceolate phialides. The chains are compact and columnar.

The metulae, structures bearing the phialides, are 8 to 9µ × 1.7 to 2.5µ and are arranged in a terminal whorl on branches. The latter, 1 to 3 in number, support the metulae and attach directly to the conidiophore. Conidiophore length and diameter, below the penicillus, range from 40 to 70µ × 2.5 to 3.0µ. The conidia, as well as the conidiophores, are smooth. Conidia are thick walled, ovoid to sub-globose in shape and 2.5µ × 2.1µ in size.

The exudate from *Penicillium funiculosum* A.T.C.C. No. 20783 on Czapek's agar is colorless, but is amber on Czapek's steep agar and is absent on malt agar. Yellow incrustations are seen on the funiculose hyphae. Sclerotia or perithecia are absent.

The above characteristics identify the organism as *Penicillium funiculosum*, as described by K. B. Raper and C. Thom in *The Manual of Penicillia*, Williams and Wilkins Co., Baltimore, Md., 1949.

Production of the Antibiotic

*Pencillium funiculosum* A.T.C.C. No. 20783 produces 4-diazo-3-methoxy-2,5-cyclohexadien-1-one. To form the product according to the preferred fermentation method, *Penicillium funiculosum* A.T.C.C. No. 20783 is grown at or near room temperature (25° C.) under submerged aerobic conditions in an aqueous nutrient medium containing assimilable sources of carbohydrates and nitrogen. The fermentation is carried out until substantial activity is imparted to the medium, usually about 72 hours.

After completion of the fermentation, the mycelia are removed from the harvested broth by filtration. The antibiotic in the filtrate is then adsorbed onto HP-20 resin in a batch fashion, and after washing the resin with water followed by acetonitrile:water (1:9, v/v), the antibiotic is eluted with acetonitrile:water (2:3, v/v). Further purification is effected by column chromatography on LPS-1 silica gel with acetonitrile:methanol (4:1, v/v) followed by column chromatography on silica gel with methanol:chloroform (1:9, v/v) and finally, by column chromatography on silica gel with acetonitrile:methanol (4:1, v/v) to yield pure product.

Alternatively, 4-diazo-3-methoxy-2,5-cyclohexadien-1-one can be synthesized chemically. First, 2-methoxy-p-benzoquinone is synthesized by the addition of m-methoxyphenol in acetone to an aqueous solution of potassium nitrosodisulfonate and potassium monobasic phosphate. On treatment of 2-methoxy-p-benzoquinone with p-toluenesulfonhydrazide, the antibiotic is produced. Purification of the product from the reaction mixture is accomplished by chromatography on a silica gel column with chloroform:methanol (9:1, v/v).

4-Diazo-3-methoxy-2,5-cyclohexadien-1-one is a weak base and will form salts with inorganic and organic acids. Illustrative salts are the hydrohalides (e.g., hydrochloride and hydrobromide), sulfate, nitrate, phosphate, tartrate, maleate, fumarate, citrate, succinate, methanesulfonate, benzenesulfonate, toluenesulfonate, and the like.

The following examples further illustrate the fermentation, isolation and chemical synthesis of 4-diazo-3-methoxy-2,5-cyclohexadien-1-one. It should be noted that the compound is photolabile (half-life<2 hours). Work with the compound was done with the lights out. The compound was stored in chloroform at −20° C. protected from light.

EXAMPLE 1

Fermentation of *Penicillium funiculosum* A.T.C.C. No. 20783

*Penicillium funiculosum* A.T.C.C. No. 20783 was maintained on Potato Dextrose Agar (Difco).

A loopful of surface growth was used to inoculate each of seven 500 ml Erlenmeyer flasks, each containing 100 ml of the following sterilized medium:

| | |
|---|---|
| Tryptone | 5.0 grams |
| Malt extract | 3.0 grams |
| Glucose | 10.0 grams |
| Yeast extract | 3.0 grams |
| Distilled water to | 1000 ml |

The medium was sterilized by autoclaving at 121° C. for 15 minutes. After inoculation, the flasks were incubated at 25° C. on a rotary shaker (300 rpm, 2 inch stroke) for approximately 96 hours. After the incubation period, 5% (v/v) transfers were made from the grown culture flasks to 100, 500 ml Erlenmeyer flasks, each containing 100 ml of the same liquid medium as used to grow the inoculum. After incubation, the flasks were once gain incubated at 25° C. on a rotary shaker (300 rpm, 2 inch stroke) for about 72 hours and then harvested.

At harvest, the contents of the flasks were pooled, and the mycelium removed by filtration. Approximately, 9.5 liters of fermentation filtrate were so obtained. To this 9.5 liters was added 600 ml of HP-20 resin (coarse grade) and the suspension was stirred at room temperature for 1.5 hours. The resin, removed from the suspension by filtration, was packed into a 5×50 cm column. After washing with water (two 1 liter portions) and then by acetonitrile:water, 1:9, v/v (five 200 ml portions), the column was eluted with acetonitrile:water 2:3, v/v (10×100 ml portions). Each fraction of the elute was assayed for bioactivity against *Escherichia coli* SGB 4, from the Culture Collection of E. R. Squibb & Sons, Inc., Princeton, N.J., by a conventional paper disc, agar diffusion assay. The bioactive fractions were combined to give about 890 ml of material which was concentrated in vacuo to 112 ml. This concentrate, adjusted to pH 5 by the addition of 1 N hydrochloric acid, was extracted five times with 100 ml aliquots of a mixture of chloroform:methanol (4:1, v/v). The extract was then concentrated in vacuo to yield 375.8 mg of a brown oil.

The brown oil, dissolved in 2 ml of acetonitrile:methanol, 4:1, v/v, was further purified by chromatography on a Whatman LPS-1 silica gel column (1.5×17 cm) packed in the same solvent. Elution of the active material was accomplished with acetonitrile:methanol, 4:1 v/v (flow rate of 2.5 ml/0.5 min). The active fractions were pooled and dried in vacuo to yield 26.6 mg of an oil. This material, dissolved in 2×0.5 ml aliquots of chloroform:methanol (9:1, v/v) was chromatographed on a silica gel column (Baker's silica gel, 1×12 cm) with chloroform:methanol, 9:1, v/v. Two ml fractions were collected. The bioactive eluates were again pooled and concentrated in vacuo to a residue (11.2 mg). This residue, dissolved in 1 ml of acetonitrile:methanol (4:1, v/v) was rechromatographed on a silica gel column (Baker's silica gel, 1×6 cm) with acetonitrile:methanol (4:1). The bioactive fractions were once again pooled and concentrated to dryness, yielding 9.4 mg of pure antibiotic as yellow crystals.

EXAMPLE 2

Chemical Synthesis of 4-diazo-3-methoxy-2,5-cyclohexadien-1-one

A solution of potassium nitrosodisulfonate (0.75 g) and potassium monobasic phosphate (0.75 g) in water (37.5 ml) was added to m-methoxyphenol (109 mg, 0.9 mmol) in acetone (12.5 ml) and the resulting mixture was stirred vigorously for 10 minutes. Potassium nitrosodisulfonate (0.75 g) was added to the reaction mixture in two portions at 30 minute intervals and the stirring was continued for an additional two hours. After removal of acetone under reduced pressure, the resulting aqueous solution was extracted with dichloromethane (four 10 ml aliquots). The combined organic layers were washed with 0.01 N sodium hydroxide (10 ml) and then with water (10 ml) and then dried over anhydrous magnesium sulfate. The dried solution was filtered and the solvents removed under reduced pressure to yield 146.1 mg of 2 -methoxy-p-benzoquinone.

An ice-cold soluton of 2 -methoxy-p-benzoquinone (69 mg, 0.5 mmol) in dichloromethane (2 ml) was added to an ice-cold solution of p-toluenesulfonhydrazide (102 mg, 0.55 mmol) in 2 ml of dichloromethane and the resulting solution was stirred at 0° C. for 1 hour. Additional p-toluenesulfonhydrazide (50 mg, 0.27 mmol) was added to the reaction mixture and the resulting mixture was stirred at 0° C. for two hours. The solvent was then removed under reduced pressure and the residue was chromatographed on a silica gel column (2.5×18 cm) with chloroform:methanol (9:1, v/v). The bioactive fractions were combined and concentrated in vacuo to give 26.7 mg of 4-diazo-3-methoxy-2,5-cyclohexadien-1-one as a yellow solid: UV max in $CH_3OH$ ($E_{1\ cm}^{1\%}$) 335 (730), 250 (120): $^1H$ NMR in $CDCl_3\delta$: 3.90 (s,3H)., 6.05 (d, 1H, 1.5 Hz), 6.30 (dd, 1H, 9.5, 1.6 Hz), 7.28 (d, 1H, 9.5 Hz); $^{13}C$ NMR in $CDCl_3\delta$: 56.4, 71.2, 103.8, 122.9, 126.7, 161.5, 182.6; IR in chloroform: 2110, 1635, 1600 $cm^{-1}$; and molecular weight by mass spectrum 150; $R_f$ equals 0.25 in a TLC system on silica gel with chloroform:methanol, 9:1, v/v, as the solvent.

Biological Activity

4-Diazo-3-methoxy-2,5-cyclohexadien-1-one, and pharmaceutically acceptable salts thereof, can be used to combat bacterial infections in mammals including humans, dogs, cats, cows and horses. All modes of administration which have been used in the past to deliver penicillins and cephalosporins to the site of the infection are contemplated for use with the compound of this invention.

The following methodology was used to determine various minimum inhibitory concentrations (hereinafter referred to as MIC) of 4-diazo-3-methoxy-2,5-cyclohexadien-1-one. The MIC is the lowest concentration of compound inhibiting growth of the test organism. All assays were done with the compound protected from light by working in a semi-darkened room.

The aerobic test organisms were grown in approximately 15–20 ml of Antibiotic Assay Broth (Difco) by inoculating (in tubes) the broth with a loopful of the organism from a BHI (Difco) agar slant. The inoculated tubes were incubated at 37° C. for 18 to 24 hours. These cultures are assumed to contain $10^9$ colony forming units (CFU) per ml. The cultures were diluted 1:100 to give a final inoculum level of $10^7$ CFU; dilutions were made with Yeast Beef Broth (Difco).

4-Diazo-3-methoxy-2,5-cyclohexadien-1-one was dissolved in an appropriate diluent at a concentration of 1,000 µg/ml. Two-fold dilutions were made in Yeast Beef Broth (Difco), resulting in a range from 1000 µg/ml to 0.05 µg/ml. 1.5 ml of each dilution was placed into individual petri dishes to which 13.5 ml of K-10 agar* was added.

*K-10 agar is composed of: Beef extract: 1.5 grams, Yeast extract: 3.0 grams, Peptone: 6.0 grams, Dextrose: 1.0 grams, Agar: 15.0 grams, Distilled water q.s. to 1 liter.

The final drug concentration in the agar ranged from 100 µg/ml to 0.05 µg/ml. Organism growth control plates containing agar only were prepared and inoculated before and after the test plates. The organisms were applied to the agar surface of each plate with a Denly Multipoint Inoculator (which delivers approximately 0.001 ml of each organism) resulting in a final inoculum of $10^4$ CFU on the agar surface.

The plates were incubated at 37° C. for 18 hours and the MIC's determined.

The agar dilution assays

| Organism | MIC (µg/ml) |
|---|---|
| Staphylococcus aureus *SC1276 | 2.5 |
| Staphylococcus aureus SC2399 | 12.5 |
| Staphylococcus aureus SC2400 | 12.5 |
| Streptococcus faecalis SC9011 | 6.3 |
| Streptococcus agalactiae SC9287 | 6.3 |
| Escherichia coli SC8294 | 3.1 |
| Escherichia coli SC10896 | 6.3 |
| Escherichia colid SC10909 | 3.1 |
| Klebsiella aerogenes SC10440 | 12.5 |
| Klebsiella pneumoniae SC9527 | 25.0 |
| Proteus mirabilis SC3855 | 3.1 |
| Salmonella typhosa SC1195 | 1.6 |
| Shigella sonnei SC8449 | 1.6 |
| Enterobacter cloacae SC8236 | 50.0 |
| Pseudomonas aeruginosa SC8333 | 25.0 |

*SC denotes organism from the culture collection of E. R. Squibb & Sons, Inc., Princeton, New Jersey.

The susceptibility of a number of anaerobic bacteria was also determined by an agar dilution technique. Test organisms were prepared from 24–48 hour cultures grown in Chopped Meat Broth (Scott Laboratories, Fiskeville, R.I.) or from washings from chocolate agar slants. These slants were prepared by adding hemoglobin to Proteose #3 Agar (Difco) to a concentration of one percent. The growth was washed off the slants with Brain Heart Infusion Broth (BBL Microbiology Systems) and diluted to a density of $10^8$ CFU/ml. The subject compound was dissolved in the appropriate diluent at a concentration of 1000 µg/ml. Two fold dilutions were made in Yeast Beef Broth (Difco) resulting in a range from 1000 µg/ml to 0.5 µg/ml. A 1.5 ml sample from each dilution was placed into individual petri dishes to which 13.5 ml of DST agar (Oxoid USA, Inc., Red Branch Road, Columbia, Md.) containing 5% lysed sheep blood and 0.5 µg/ml vitamin K was added. The final drug concentration in the agar ranged from 1000 µg/ml to 0.05 µg/ml. Organism growth control plates containing agar only were prepared and inoculated before and after the test plates. The organisms were applied to the surface of each plate with the Denyl Multipoint Inoculator, which delivers approximately 0.001 ml of each organism, resulting in a final inoculum level of $10^5$ CFU on the agar surface. Plates were incubated at 37° C. for 18 hours in an anaerobic chamber (Forma Scientific, Marietta, Ohio) and the MIC values then determined.

The agar dilution assays yielded the following results:

| Organism | MIC (µg/ml) |
|---|---|
| Bacteroides thetaiotamicron SC9005 | 0.4 |
| Bacteroides thetaiotamicron SC10278 | 0.4 |
| Bacteroides fragilis SC9844 | 0.4 |
| Bacteroides fragilis SC10277 | 0.4 |
| Bacteroides fragilis SC11085 | 0.2 |
| Clostridium histolyticum SC8572 | 0.1 |
| Clostridium perfringens SC11256 | 0.2 |
| Clostridium septicum SC1780 | <0.05 |
| Clostridium difficile SC11251 | 0.4 |
| Hemophilus vaginalis SC8568 | 0.2 |
| Hemophilus vaginalis SC9640 | 0.4 |
| Fusobacterium necrophorum SC10338 | <0.05 |
| Pseudomonas anaerobius SC11263 | <0.05 |

What is claimed is:
1. 4-Diazo-3-methoxy-2,5-cyclohexadien-1-one, or a pharmaceutically acceptable salt thereof.
2. 4-Diazo-3-methoxy-2,5-cyclohexadien-1-one.

* * * * *